(12) United States Patent
Huang et al.

(10) Patent No.: US 11,407,710 B2
(45) Date of Patent: Aug. 9, 2022

(54) METHOD FOR PREPARING AN N-CYCLOPROPYLMETHYL ANILINE COMPOUND

(71) Applicant: JIANGXI UNIVATE NEW MATERIAL CO., LTD., Ji'an (CN)

(72) Inventors: Chaoqun Huang, Ji'an (CN); Jintao Zhu, Ji'an (CN); Liang Lv, Ji'an (CN); Liangming Luo, Ji'an (CN); Rong Zhang, Ji'an (CN); Jiyong Liu, Ji'an (CN)

(73) Assignee: JIANGXI UNIVATE NEW MATERIAL CO., LTD.

( * ) Notice: Subject to any disclaimer, the term of this patent is extended or adjusted under 35 U.S.C. 154(b) by 0 days.

(21) Appl. No.: 17/541,346

(22) Filed: Dec. 3, 2021

(65) Prior Publication Data
US 2022/0177414 A1 Jun. 9, 2022

(30) Foreign Application Priority Data
Dec. 4, 2020 (CN) .......................... 202011409042.2

(51) Int. Cl.
*C07C 221/00* (2006.01)
(52) U.S. Cl.
CPC .................. *C07C 221/00* (2013.01)

(58) Field of Classification Search
CPC ... C07C 221/00; C07C 225/22; C07C 229/60; A01N 37/18
See application file for complete search history.

(56) References Cited

U.S. PATENT DOCUMENTS

| 7,253,198 | B2 * | 8/2007 | Demont | C07D 409/12 |
| | | | | 514/424 |
| 7,390,908 | B2 * | 6/2008 | Boyd | C07D 233/48 |
| | | | | 548/161 |
| 7,951,830 | B2 * | 5/2011 | Boyd | C07D 213/85 |
| | | | | 514/252.12 |
| 10,981,861 | B1 * | 4/2021 | Zhu | C07C 315/04 |
| 11,180,443 | B2 * | 11/2021 | Zhu | C07C 231/14 |
| 2020/0178525 | A1 * | 6/2020 | Lv | C07C 255/50 |
| 2022/0081389 | A1 * | 3/2022 | Liu | A01N 37/18 |

FOREIGN PATENT DOCUMENTS

| EP | 3812366 A1 * | 4/2021 | ........... C07C 201/12 |
| WO | WO-03015774 A1 * | 2/2003 | ........... A61K 31/165 |
| WO | WO-2004050619 A1 * | 6/2004 | ......... C07D 207/267 |
| WO | WO-2021078293 A1 * | 4/2021 | |

* cited by examiner

*Primary Examiner* — Alexander R Pagano
(74) *Attorney, Agent, or Firm* — Dilworth IP, LLC

(57) ABSTRACT

Provided is a method for preparing an N-cyclopropylmethyl aniline compound, which comprises hydrogenating a compound represented by Formula II and cyclopropyl formaldehyde as raw materials in the presence of an acid and catalyst to generate an N-cyclopropylmethyl aniline compound represented by Formula I, wherein R is alkoxy, alkylamino or a substituted anilino group represented by Formula III.

30 Claims, No Drawings

METHOD FOR PREPARING AN N-CYCLOPROPYLMETHYL ANILINE COMPOUND

TECHNICAL FIELD

The present disclosure belongs to the field of the synthesis of pesticides and insecticide compounds, and relates to a method for preparing an N-cyclopropylmethyl aniline compound.

The present disclosure specifically relates to a "one-pot method" for preparing an N-cyclopropylmethyl aniline compound, and particularly relates to a preparation having the advantages of low cost, clean production, high yield, simple operation, etc.

BACKGROUND

N-cyclopropylmethyl aniline is an important intermediate for preparing an m-diamide compound. As reported recently, in the synthesis of the meta-diamide insecticide cyproflanilide (CAS: 2375110-88-4), it is necessary to use this type of intermediate, particularly a compound having the following general formula I:

wherein R is alkoxy, alkylamino or a substituted anilino group (i.e., 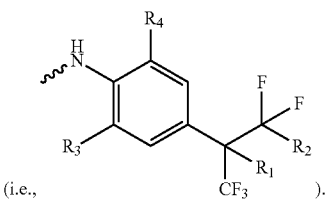 ).

The prior art discloses some reports on the preparation of N-cyclopropylmethyl aniline compounds. For example, CN109497062A discloses a method in which bromomethyl cyclopropane is reacted with substituted aniline to obtain N-cyclopropylmethyl aniline compound A according to the scheme as follows:

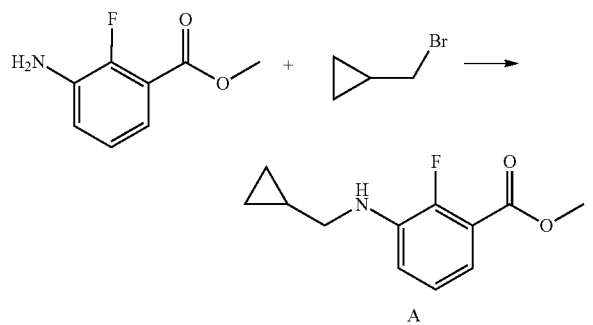

A

This method takes a long reaction time (16 h), and has a low yield rate (49%) and complicated post-processing. And the bromomethyl cyclopropane used is expensive.

CN110028423A discloses a method in which a boron reagent and cyclopropyl formaldehyde are reacted with substituted aniline in a system of trifluoroacetic acid to prepare N-cyclopropylmethyl aniline compound B according to the scheme as follows:

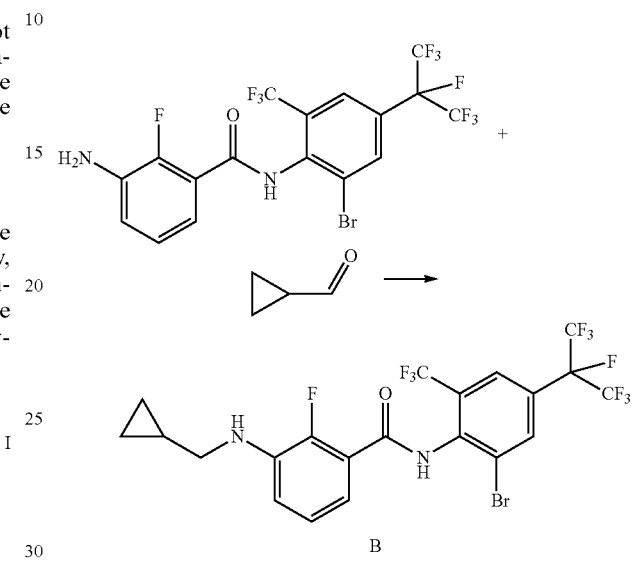

B

The boron reagent (sodium triacetoxyborohydride) and the trifluoroacetic acid are expensive, a large number of di-substituted compounds are produced during the reaction, and the yield rate is low.

The US patent (U.S. Ser. No. 16/837,419) discloses the reaction of cyclopropyl formaldehyde with substituted aniline in a zinc powder-acetic acid system to prepare N-cyclopropylmethyl aniline compound C. The scheme is as follows:

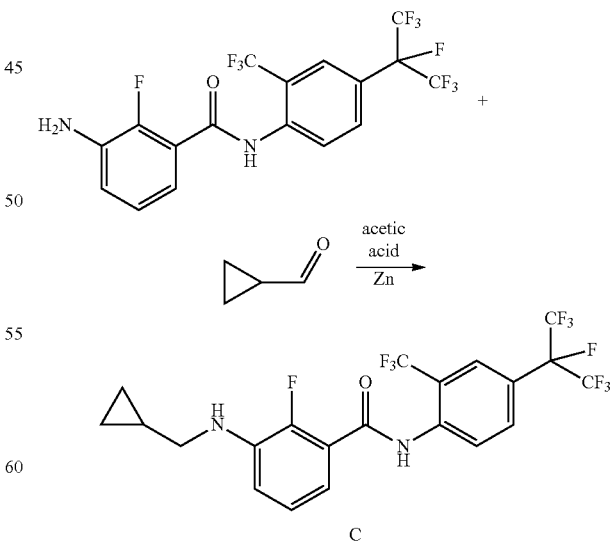

C

Although this method has a high yield, metal zinc powder is used in the reaction process, which will produce a large amount of solid slags, making post-treatment difficult.

Therefore, in the art, it is desired to develop a method for preparing an N-cyclopropylmethyl aniline compound with low cost, clean production, high yield, and simple operation.

SUMMARY

To overcome the disadvantages of the related art, the present disclosure aims to provide a method for preparing an N-cyclopropylmethyl aniline compound. Specifically, provided is a method for preparing an N-cyclopropylmethyl aniline compound by adopting a "one-pot method". In particular, provided is a preparation method of N-cyclopropylmethyl aniline compounds with low cost, clean production, high yield and simple operation.

To achieve this object, the present disclosure adopts the technical solutions described below.

The present disclosure provides a method for preparing an N-cyclopropylmethyl aniline compound, which includes the following steps:

The compound represented by Formula II and cyclopropyl formaldehyde are used as raw materials, and the hydrogenation reaction is carried out under the action of an acid and a catalyst to obtain the N-cyclopropylmethyl aniline compound represented by Formula I. The scheme is as follows:

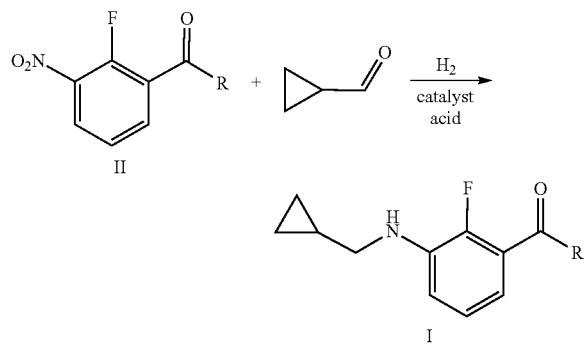

wherein R is selected from alkoxy, alkylamino or a substituted anilino group represented by Formula III:

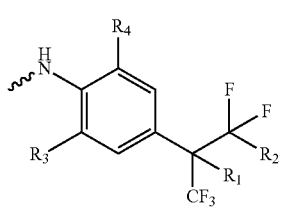

wherein $R_1$ is selected from methoxy or fluorine, $R_2$ is selected from fluorine or trifluoromethyl, $R_3$ is selected from any one of H, fluorine, chlorine, bromine, iodine, nitro or trifluoromethyl, and $R_4$ is selected from any one of trifluoromethyl, trifluoromethoxy or difluoromethoxy; and ⁓ represents the position at which the group is attached.

The preparation method involved in the present disclosure utilizes the compound of Formula II and cyclopropyl formaldehyde as raw materials, and adopts the "one-pot method" to carry out the two-step reaction of nitro reduction and amino alkylation through the method of catalytic hydrogenation, which reduces post-treatment operations. The method also has the advantages of simplified operation, low cost and clean manufacturing. The reaction yield is improved and the method is suitable for industrial production at the same time. In the preparation method of the present disclosure, fewer impurities are produced, so that a high yield rate of products is achieved. A product with a high purity may be obtained by simple post-processing without performing complicated and tedious post-processing.

In the present disclosure, as a preferred technical solution, R is selected from any one of C1-C6 alkoxy (for example, C1, C2, C3, C4, C5 or C6 alkoxy), preferably methoxy, ethoxy, propoxy or isopropoxy.

In the present disclosure, as a preferred technical solution, R is selected from any one of C1-C6 alkylamino (for example, C1, C2, C3, C4, C5 or C6 alkylamino), preferably methylamino.

In the present disclosure, as a preferred technical solution, R is selected from a substituted anilino group represented by Formula III:

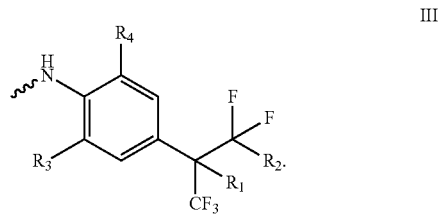

wherein $R_1$ is fluorine, $R_2$ is fluorine, $R_3$ is selected from any one of H, bromine or iodine, and $R_4$ is selected from any one of trifluoromethyl, trifluoromethoxy or difluoromethoxy; and ⁓ represents the position at which the group is attached.

In the present disclosure, the hydrogenation reaction is carried out in a solvent, and the solvent includes any one or a combination of at least two of alcohol solvents, ester solvents, ether solvents, halogenated hydrocarbon solvents or benzene solvents.

The combination of at least two is, for example, a combination of an alcohol solvent and an ester solvent, a combination of an ester solvent and an ether solvent, etc. Any other combination mode can be selected, which will not be exhaustively listed in the present disclosure.

Preferably, the alcohol solvent includes any one or a combination of at least two of methanol, ethanol, or isopropanol. The combination of at least two is, for example, a combination of methanol and ethanol, a combination of ethanol and isopropanol, a combination of methanol and isopropanol, etc. Any other combination can be selected, which will not be exhaustively listed in the present disclosure.

Preferably, the ester solvent includes any one or a combination of at least two of methyl acetate, ethyl acetate, propyl acetate or butyl acetate. The combination of at least two is, for example, a combination of methyl acetate and ethyl acetate, a combination of ethyl acetate and propyl acetate, etc. Any other combination can be selected, which will not be exhaustively listed in the present disclosure.

Preferably, the ether solvent includes any one or a combination of at least two of diethyl ether, methyl tert-butyl ether or tetrahydrofuran. The combination of at least two is, for example, a combination of diethyl ether and methyl tert-butyl ether, a combination of methyl tert-butyl ether and tetrahydrofuran, etc. Any other combination can be selected, which will not be exhaustively listed in the present disclosure.

Preferably, the halogenated hydrocarbon solvent includes dichloromethane and/or dichloroethane.

Preferably, the benzene solvent includes toluene and/or xylene.

Preferably, the solvent is any one or a combination of at least two of methanol, ethanol, ethyl acetate or toluene. The combination of at least two is, for example, a combination of methanol and ethanol, a combination of ethyl acetate and toluene, a combination of ethanol and ethyl acetate, etc. Any other combination can be selected, which will not be exhaustively listed in the present disclosure.

The reaction solvent involved in the present disclosure is preferably any one or a combination of at least two of methanol, ethanol, ethyl acetate or toluene because the reaction conditions in these solvents are good and the solvents are easy to recover and process.

In the present disclosure, the acid includes inorganic acid or organic acid.

Preferably, the acid is any one or a combination of at least two of formic acid, acetic acid, propionic acid, hydrochloric acid, or sulfuric acid. The combination of at least two is, for example, a combination of formic acid and acetic acid, a combination of hydrochloric acid and sulfuric acid, etc. Any other combination can be selected, which will not be exhaustively listed in the present disclosure.

Preferably, the acid is acetic acid and/or propionic acid.

The acid involved in the present disclosure is more preferably acetic acid and/or propionic acid because the reaction effect of acetic acid and/or propionic acid is the best.

In the present disclosure, the catalyst includes any one of palladium carbon, platinum carbon or Raney nickel; preferably platinum carbon.

The reaction catalyst involved in the present disclosure is more preferably platinum carbon because of its best reaction effect.

Preferably, the molar ratio of the compound represented by Formula II to the cyclopropyl formaldehyde is 1:(0.5-3), for example, 1:0.5, 1:1, 1:1.2, 1:1.5, 1:1.6, 1:2, 1:2.5, 1:3, preferably is 1:(1.2-1.6), and other specific point values within the above numerical range can be selected, which will not be exhaustively listed in the present disclosure.

Preferably, the mass ratio of the compound represented by Formula II to the acid is 1:(0.01-0.6), for example, 1:0.01, 1:0.05, 1:0.1, 1:0.2, 1:0.3, 1:0.4 or 1:0.6, preferably is 1:(0.05-0.4), and other specific point values within the above numerical range can be selected, which will not be exhaustively listed in the present disclosure.

The mass ratio of the compound represented by Formula II to the acid is specifically selected to be in the numerical range of 1:(0.01-0.6) because if the added amount of acid is further increased, resources will be wasted and the cost will be increased; and if the added amount of acid is further reduced, it will make the raw materials incompletely react.

Preferably, the mass ratio of the compound represented by Formula II to the catalyst is 1:(0.001-0.05), for example, 1:0.001, 1:0.002, 1:0.005, 1:0.01, 1:0.02, 1:0.03, 1:0.04, or 1:0.05, preferably is 1:(0.005-0.02), and other specific point values within the above numerical range can be selected, which will not be exhaustively listed in the present disclosure.

The mass ratio of the compound represented by Formula II to the acid is specifically selected to be in the numerical range of 1:(0.001-0.05) because if the added amount of catalyst is further increased, resources will be wasted and the cost will be increased; and if the added amount of catalyst reduced, it will make the raw materials incompletely react.

Preferably, the mass ratio of the compound represented by Formula II to the solvent is 1:(2-10), for example, 1:2, 1:3, 1:4, 1:5, 1:6, 1:7, 1:8, 1:9, or 1:10, preferably is 1:(3-8), and other specific point values within the above numerical range can be selected, which will not be exhaustively listed in the present disclosure.

In the present disclosure, the hydrogenation reaction is carried out at a temperature of 30-150° C., such as 30° C., 40° C., 50° C., 60° C., 80° C., 100° C., 120° C. or 150° C., etc., preferably 40-100° C.; and the hydrogenation reaction is carried out for 8-20 h, preferably 12-16 h, such as 8 h, 10 h, 12 h, 14 h, 15 h, 16 h, 17 h, 18 h, 19 h or 20 h, etc., and other specific point values within the above numerical range can be selected, which will not be exhaustively listed in the present disclosure.

Preferably, in the hydrogenation reaction, the pressure after introducing hydrogen is controlled to be 0.2-5.0 MPa, such as 0.2 MPa, 0.5 MPa, 1.0 MPa, 2.0 MPa, 3.0 MPa, 4.0 MPa or 5.0 MPa, etc., preferably 1.0-3.0 MPa. Other specific point values within the above numerical range can be selected, which will not be exhaustively listed in the present disclosure.

As a preferred technical solution of the present disclosure, the preparation method of the N-cyclopropylmethyl aniline compound specifically includes the following steps:

Taking the compound represented by Formula II and cyclopropyl formaldehyde as raw materials, under the action of an acid and a catalyst, the hydrogenation reaction is carried out at 30-150° C. for 8-20 h, and the pressure is controlled at 0.2-5.0 MPa to obtain the N-cyclopropylmethyl aniline compound represented by Formula I. The scheme is as follows:

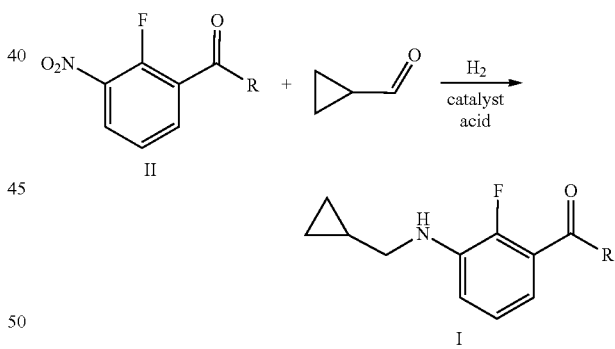

wherein, the limited range of R is consistent with claim 1; the molar ratio of the compound represented by Formula II to cyclopropyl formaldehyde is 1:(0.5-3); the mass ratio of compound represented by Formula II to the acid is 1:(0.01-0.6); the mass ratio of the compound of Formula II to the catalyst is 1:(0.001-0.05); and the mass ratio of the compound of Formula II to the solvent is 1:(2-10).

Compared with the existing art, the present disclosure has the following beneficial effects:

The preparation method involved in the present disclosure utilizes the compound of formula II and cyclopropyl formaldehyde as raw materials, through the method of catalytic hydrogenation, the two-step reaction of nitro reduction and amino alkylation is carried out by the "one-pot method", which reduces post-processing operations. The process is simple, the operation is simple, the cost is low, the production is clean, and the yield of the reaction is improved at the same time, so the method is suitable for industrial production. The preparation method produces few impurities, so that the product yield is high, and the product can be obtained with relatively high purity after simple post-treatment, without complicated and tedious post-treatment.

DETAILED DESCRIPTION

In order to further illustrate the technical means adopted by the present disclosure and its effects, the technical solutions of the present disclosure will be further described below in conjunction with preferred embodiments of the present disclosure, but the present disclosure is not limited to the scope of the embodiments.

EXAMPLE 1

In this Example, methyl 3-[(cyclopropylmethyl)amino]-2-fluorobenzoate was prepared according to the following scheme:

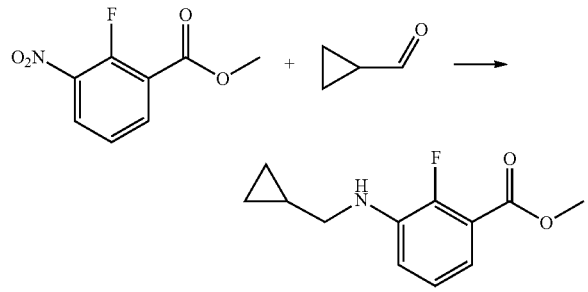

In a 500 mL autoclave, 40.2 g (0.2 mol, purity 99%) of methyl 2-fluoro-3-nitrobenzoate, 0.2 g of 5% platinum carbon catalyst, 7.96 g (0.13 mol, purity 99%) of acetic acid, 16.8 g of cyclopropyl formaldehyde (0.24 mol, purity 99%) and 119.4 g of methanol were sequentially added. Hydrogen was introduced to a pressure of 1.0 MPa, and reacted at 40° C. for 12 h. After the reaction, the reaction solution was filtered, and the filter residue was washed with 20 g methanol. The filtrate was combined, and the solvent was removed under reduced pressure. The resultant was dried to obtain 43.2 g of methyl 3-[(cyclopropylmethyl)amino]-2-fluorobenzoate with a content of 98.5% (external standard method, the same below) and a yield of 95.4% (mass yield, the same below).

Characterization data: LC/MS [M+1]: m/z=224.

$^1$H NMR (400 MHz, CDCl$_3$) data (δ[ppm]): 7.18-7.15 (m, 1H), 7.05-7.01 (m, 1H), 6.85-6.82 (m, 1H), 4.21 (br s, 1H), 3.93 (s, 3H), 3.01 (d, J=5.6 Hz, 2H), 1.15-1.12 (m, 1H), 0.62-0.58 (m, 2H), 0.30-0.25 (m, 2H).

EXAMPLE 2

In this Example, ethyl 3-[(cyclopropylmethyl)amino]-2-fluorobenzoate was prepared according to the following scheme:

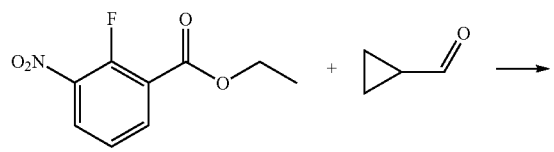

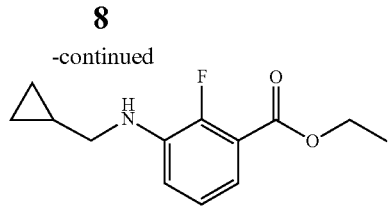

In a 500 mL autoclave, 43.0 g (0.2 mol, purity 99%) of ethyl 2-fluoro-3-nitrobenzoate, 0.42 g of 5% platinum carbon catalyst, 8.52 g (0.14 mol, purity 99%) of acetic acid, 19.6 g of cyclopropyl formaldehyde (0.28 mol, purity 99%) and 213 g of ethanol were sequentially added. Hydrogen was introduced to a pressure of 2.0 MPa, and reacted at 60° C. for 14 h. After the reaction, the reaction solution was filtered and the filter residue was wash with 20 g ethanol. The filtrate was combined, and the solvent was removed under reduced pressure. The resultant was dried to obtain 45.1 g of ethyl 3-[(cyclopropylmethyl)amino]-2-fluorobenzoate with a content of 98.0% and a yield of 95.4%.

Characterization data: LC/MS [M+1]: m/z=238.

EXAMPLE 3

In this Example, propyl 3-[(cyclopropylmethyl)amino]-2-fluorobenzoate was prepared according to the following scheme:

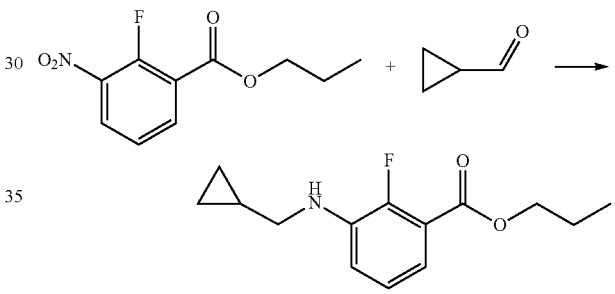

In a 500 mL autoclave, 45.9 g (0.2 mol, purity 99%) of propyl 2-fluoro-3-nitrobenzoate, 0.91 g of 5% platinum carbon catalyst, 18.16 g (0.30 mol, purity 99%) of acetic acid, 22.4 g of cyclopropyl formaldehyde (0.32 mol, purity 99%) and 136.2 g of ethyl acetate were sequentially added. Hydrogen was introduced to a pressure of 3.0 MPa, and reacted at 100° C. for 16 h. After the reaction, the reaction solution was filtered and the filter residue was washed with 20 g ethyl acetate. The filtrate was combined, and the solvent was removed under reduced pressure. The resultant was dried to obtain 48.5 g of propyl 3-[(cyclopropylmethyl)amino]-2-fluorobenzoate with a content of 97.5% and a yield of 94.2%.

Characterization data: LC/MS [M+1]1: m/z=252.

EXAMPLE 4

In this Example, isopropyl 3-[(cyclopropylmethyl)amino]-2-fluorobenzoate was prepared according to the following scheme:

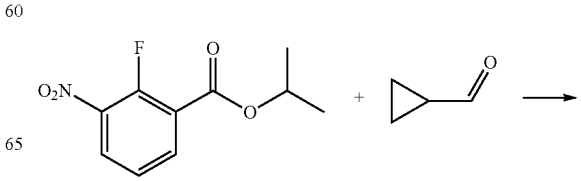

-continued

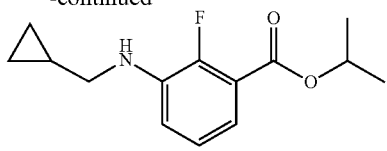

In a 500 mL autoclave, 45.9 g (0.2 mol, purity 99%) of isopropyl 2-fluoro-3-nitrobenzoate, 0.91 g of 5% platinum carbon catalyst, 9.08 g (0.15 mol, purity 99%) of acetic acid, 16.8 g of cyclopropyl formaldehyde (0.24 mol, purity 99%) and 227 g of ethyl acetate were sequentially added. Hydrogen was introduced to a pressure of 2.0 MPa, and reacted at 60° C. for 12 h. After the reaction, the reaction solution was filtered and the filter residue was washed with 20 g ethyl acetate. The filtrate was combined, and the solvent was removed under reduced pressure. The resultant was dried to obtain 48.0 g of isopropyl 3-[(cyclopropylmethyl)amino]-2-fluorobenzoate with a content of 97.8% and a yield of 93.5%.

EXAMPLE 5-1

In this Example, an N-cyclopropylmethyl aniline compound was prepared according to the following scheme:

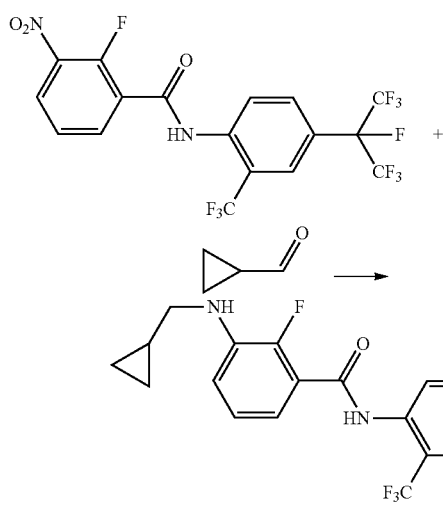

In a 500 mL autoclave, 50.1 g (0.1 mol, purity 99%) of 2-fluoro-3-nitro-N-(4-(perfluoropropan-2-yl)-2-(trifluoromethyl)phenyl)benzamide, 0.49 g of 5% platinum carbon catalyst, 2.48 g (0.03 mol, purity 99%) of propionic acid, 9.8 g of cyclopropyl formaldehyde (0.14 mol, purity 99%) and 248 g of methanol were sequentially added. Hydrogen was introduced to a pressure of 3.0 MPa, and reacted at 40° C. for 16 h. After the reaction, the reaction solution was filtered, and the filter residue was washed with 20 g methanol. The filtrate was combined, and the solvent was removed under reduced pressure. After drying, 50.4 g solid was obtained with a content of 98.4% and a yield of 95.4%.

Characterization data: LC/MS [M+1]: m/z=521.

$^1$H NMR(400 MHz, DMSO-d6) data (δ[ppm]): 10.18 (s, 1H), 8.12-8.07 (m, 1H), 8.04 (d, J=8.7 Hz, 1H), 7.92 (s, 1H), 7.10 (t, J=7.9 Hz, 1H), 6.94 (t, J=8.2 Hz, 1H), 6.90-6.82 (m, 1H), 5.82-5.72 (m, 1H), 3.03 (t, J=6.2 Hz, 2H), 1.12-1.08 (m, 1H), 0.50-0.42 (m, 2H), 0.24 (q, J=4.4 Hz, 2H).

EXAMPLE 5-2

In this Example, an N-cyclopropylmethyl aniline compound was prepared according to the following scheme:

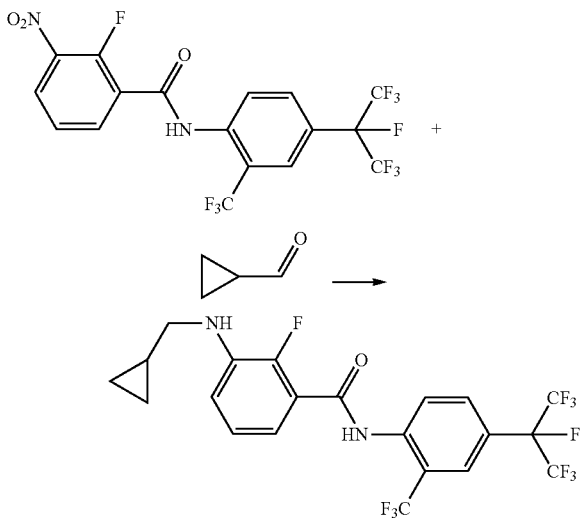

The preparation method differs from that of Example 5-1 only in that 0.49 g of the 5% platinum-carbon catalyst was replaced with a 5% palladium-carbon catalyst with equal mass, and other conditions remained unchanged. The yield was 81.2%.

EXAMPLE 5-3

In this Example, an N-cyclopropylmethyl aniline compound was prepared according to the following scheme:

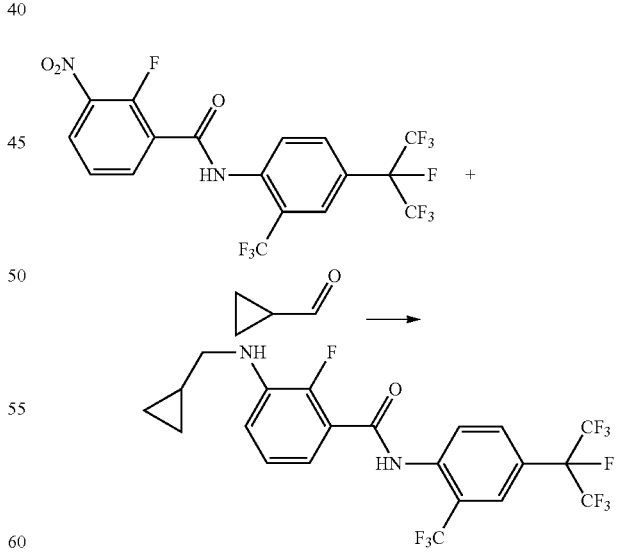

The preparation method differs from that of Example 5-1 only in that 0.49 g of the 5% platinum-carbon catalyst was replaced with a 5% Raney nickel catalyst with equal mass, and other conditions remained unchanged. The yield was 73.5%.

EXAMPLE 5-4

In this Example, an N-cyclopropylmethyl aniline compound was prepared according to the following scheme:

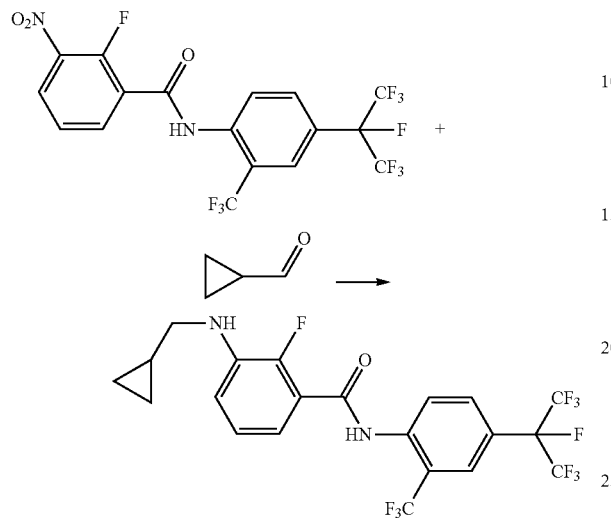

The preparation method differs from that of Example 5-1 only in that 2.48 g of propionic acid was replaced with formic acid with equal mass, and other conditions remain unchanged. The yield was 83.6%.

EXAMPLE 5-5

In this Example, an N-cyclopropylmethyl aniline compound was prepared according to the following scheme:

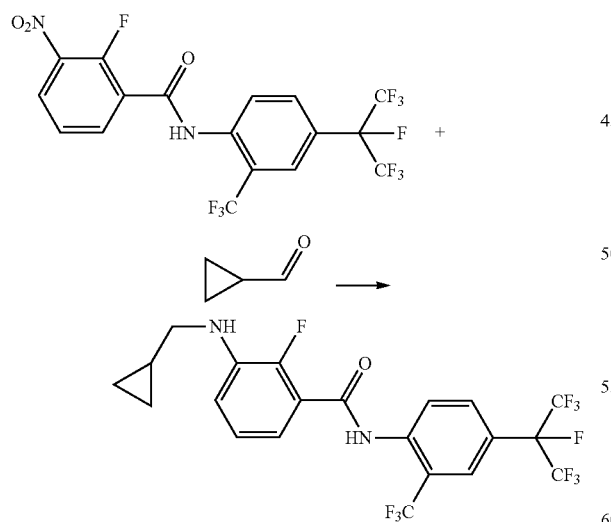

The preparation method differs from that of Example 5-1 only in that: 2.48 g of propionic acid was replaced by 36% hydrochloric acid with equal mass, and other conditions remained unchanged. The yield was 56.2%.

EXAMPLE 6

In this Example, an N-cyclopropylmethyl aniline compound was prepared according to the following scheme:

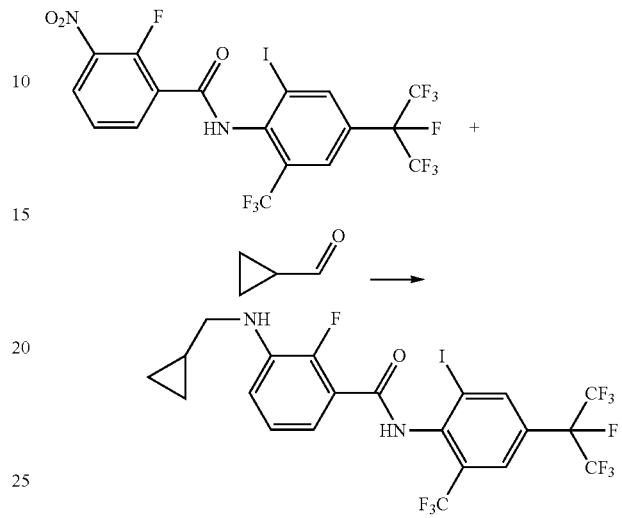

In a 500 mL autoclave, 62.8 g (0.1 mol, purity 99%) of 2-fluoro-N-(2-iodo-4-(perfluoropropan-2-yl)-6-(trifluoromethyl)phenyl)-3-nitrobenzamide, 0.62 g of 5% platinum carbon catalyst, 12.44 g (0.21 mol, purity 99%) of acetic acid, 11.2 g of cyclopropyl formaldehyde (0.16 mol, purity 99%) and 311 g of toluene were sequentially added. Hydrogen was introduced to a pressure of 1.0 MPa and reacted at 60° C. for 14 h. After the reaction, the reaction solution was filtered, and the filter residue was washed with 20 g toluene. The filtrate was combined, and the solvent was removed under reduced pressure. After drying, 62.6 g solid was obtained with a content of 97.6% and a yield of 94.6%.

Characterization data: LC/MS [M+1]: m/z=647.

$^1$H NMR(400 MHz, DMSO-d6) data (δ[ppm]): 10.53 (s, 1H), 8.41 (s, 1H), 7.97 (s, 1H), 7.11 (m, 1H), 6.96-6.91 (m, 1H), 6.84-6.81 (m, 1H), 5.79-5.75 (m, 1H), 3.04 (t, J=6.2 Hz, 2H), 1.15-1.07 (m, 1H), 0.49-0.44 (m, 2H), 0.28-0.24 (m, 2H).

EXAMPLE 7

In this Example, an N-cyclopropylmethyl aniline compound was prepared according to the following scheme:

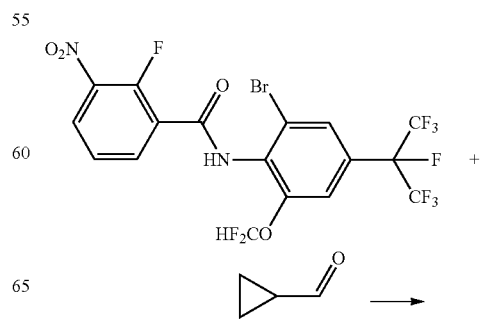

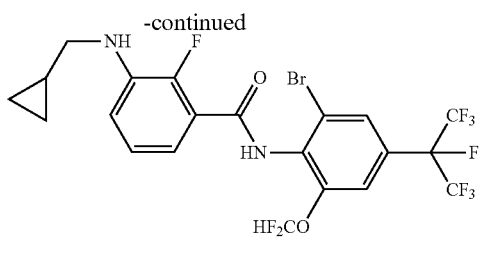

In a 500 mL autoclave, 57.9 g (0.1 mol, purity 99%) of N-(2-bromo-6-(difluoromethoxy)-4-(perfluoropropan-2-yl)phenyl)-2-fluoro-3-nitrobenzamide, 0.29 g of 5% platinum carbon catalyst, 2.86 g (0.038 mol, purity 99%) of propionic acid, 9.8 g of cyclopropyl formaldehyde (0.14 mol, purity 99%) and 171.6 g of ethyl acetate were sequentially added. Hydrogen was introduced to a pressure of 2.0 MPa, and reacted at 100° C. for 16 h. After the reaction, the reaction solution was filtered, and the filter residue was washed with 20 g ethyl acetate. The filtrate was combined, and the solvent was removed under reduced pressure. After drying, 57.8 g solid was obtained with a content of 98.0% and a yield of 94.9%.

Characterization data: LC/MS [M+1]: m/z=598.

$^1$H NMR(400 MHz, DMSO-d6) data (δ[ppm]): $^1$H NMR (400 MHz, DMSO-d6) 10.01 (s, 1H), 7.66 (s, 1H), 7.30 (s, 1H), 7.09 (t, J=72.0 Hz, 1H), 6.85 (t, J=7.8 Hz, 1H), 6.69 (t, J=7.7 Hz, 1H), 6.56 (t, J=6.2 Hz, 1H), 5.47 (s, 1H), 2.79 (t, J=5.7 Hz, 2H), 0.90-0.80 (m, 1H), 0.24-0.18 (m, 2H), 0.01 (q, J=4.9 Hz, 2H).

EXAMPLE 8

In this Example, an N-cyclopropylmethyl aniline compound was prepared according to the following scheme:

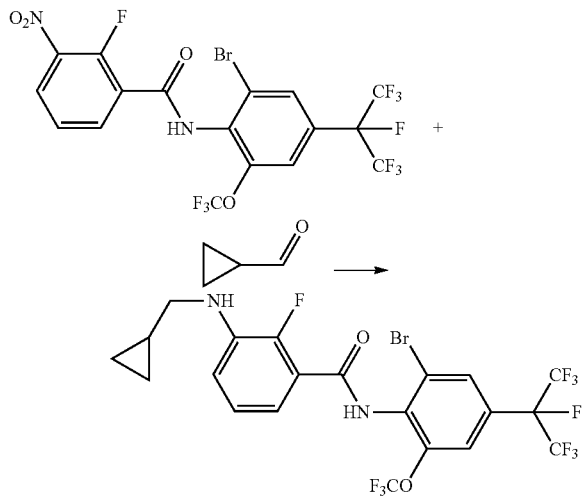

In a 1000 mL autoclave, 59.7 g (0.1 mol, purity 99%) of N-(2-bromo-4-(perfluoropropan-2-yl)-6-(trifluoromethoxy)phenyl)-2-fluoro-3-nitrobenzamide, 1.18 g of 5% platinum carbon catalyst, 23.6 g (0.39 mol, purity 99%) of acetic acid, 9.8 g of cyclopropyl formaldehyde (0.14 mol, purity 99%) and 472 g of methanol were sequentially added. Hydrogen was introduced to a pressure of 3.0 MPa, and reacted at 60° C. for 12 h. After the reaction, the reaction solution was filtered, and the filter residue was washed with 20 g methanol. The filtrate was combined, and the solvent was removed under reduced pressure. After drying, 59.7 g solid was obtained with a content of 98.2% and a yield of 95.3%.

Characterization data: LC/MS [M+1]1: m/z=616.

$^1$H NMR(400 MHz, DMSO-d6) data (δ[ppm]): 10.53 (s, 1H), 8.10 (s, 1H), 7.78 (s, 1H), 7.13-7.07 (m, 1H), 6.96-6.91 (m, 1H), 6.78-6.75 (m, 1H),5.78-5.74 (m, 1H), 3.03 (t, J=6.2 Hz, 2H), 0.98-0.90 (m, 1H), 0.26-0.22 (m, 2H), 0.16-0.12 (m, 2H).

EXAMPLE 9

In this Example, an N-cyclopropylmethyl aniline compound was prepared according to the following scheme:

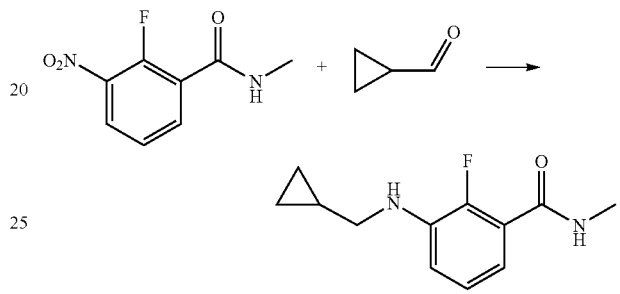

In a 500 mL autoclave, 40.0 g (0.2 mol, purity 99%) of 2-fluoro-N-methyl-3-nitrobenzamide, 0.2 g of 5% platinum carbon catalyst, 7.96 g (0.13 mol, purity 99%) of acetic acid, 16.8 g of cyclopropyl formaldehyde (0.24 mol, purity 99%) and 119.4 g of methanol were sequentially added. Hydrogen was introduced to a pressure of 1.0 MPa, and reacted at 40° C. for 12 h. After the reaction, the reaction solution was filtered, and the filter residue was washed with 20 g methanol. The filtrate was combined, and the solvent was removed under reduced pressure. After drying, 42.8 g solid was obtained with a content of 98.5% and a yield of 94.9%.

Applicant has stated that although the preparation method for the N-cyclopropylmethyl aniline compound of the present disclosure is described through the embodiments described above, the present disclosure is not limited to the embodiments described above, which means that implementation of the present disclosure does not necessarily depend on the embodiments described above. It should be apparent to those skilled in the art that any improvements made to the present disclosure, and equivalent replacements of various raw materials, the addition of adjuvant ingredients and the selection of specific manners, etc. in the present disclosure all fall within the protection scope and the scope of disclosure of the present disclosure.

The preferred embodiments of the present disclosure are described in detail above. However, the present disclosure is not limited to the specific details in the above-mentioned embodiments. Within the scope of the technical concept of the present disclosure, various simple modifications can be made to the technical solution of the present disclosure. These simple modifications all belong to the protection scope of the present disclosure.

In addition, it should be noted that the various specific technical features described in the above specific embodiments can be combined in any suitable manner without contradiction. In order to avoid unnecessary repetition, the combination method will not be explained separately.

What is claimed is:

1. A method for preparing an N-cyclopropylmethyl aniline compound, comprising:

hydrogenating a compound represented by Formula II and cyclopropyl formaldehyde as raw materials in the presence of an acid and a catalyst to generate an N-cyclopropylmethyl aniline compound represented by Formula I according to the scheme as follows:

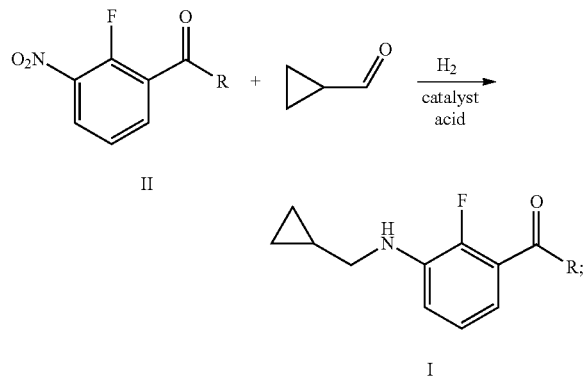

wherein R is selected from alkoxy, alkylamino or a substituted anilino group represented by Formula III:

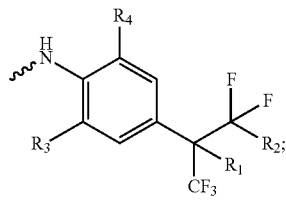

wherein $R_1$ is selected from methoxy or fluorine, $R_2$ is selected from fluorine or trifluoromethyl, $R_3$ is selected from any one of H, fluorine, chlorine, bromine, iodine, nitro or trifluoromethyl, and $R_4$ is selected from any one of trifluoromethyl, trifluoromethoxy or difluoromethoxy; and ~ represents the position at which the group is attached.

2. The method according to claim 1, wherein
R is selected from any one of C1-C6 alkoxy groups; or
R is selected from any one of C1-C6 alkylamino groups; or
R is selected from a substituted anilino group represented by Formula III

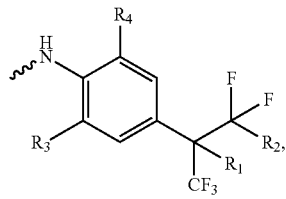

wherein $R_1$ is fluorine, $R_2$ is fluorine, $R_3$ is selected from any one of H, bromine or iodine, and $R_4$ is selected from any one of trifluoromethyl, trifluoromethoxy or difluoromethoxy; and ~ represents the position at which the group is attached.

3. The method according to claim 1, wherein the hydrogenation is carried out in a solvent which is any one or a combination of at least two selected from the group consisting of an alcohol solvent, an ester solvent, an ether solvent, a halogenated hydrocarbon solvent or a benzene solvent.

4. The method according to claim 3, wherein the alcohol solvent includes any one or a combination of at least two selected from the group consisting of methanol, ethanol and isopropanol.

5. The method according to claim 1, wherein the acid includes inorganic acids or organic acids.

6. The method according to claim 1, wherein the catalyst includes any one of palladium carbon, platinum carbon or Raney nickel.

7. The method according to claim 1, wherein the molar ratio of the compound represented by Formula II to cyclopropyl formaldehyde is 1:(0.5-3).

8. The method according to claim 1, wherein the hydrogenation reaction is carried at a temperature of 30-150° C., for 8-20 h.

9. The method according to claim 1, wherein the pressure of the hydrogenation reaction after introducing hydrogen gas is controlled to be 0.2-5.0 MPa.

10. The method according to claim 1, comprising: hydrogenating a compound represented by Formula II and cyclopropyl formaldehyde as raw materials in the presence of an acid and a catalyst under the pressure of 0.2-5.0 MPa at 30° C. to 150° C. for 8 to 20 hours to generate an N-cyclopropylmethyl aniline compound represented by Formula I according to the scheme as follows:

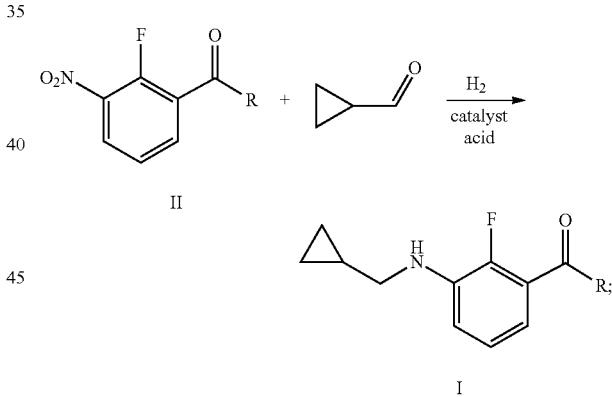

wherein
R is selected from alkoxy, alkylamino or a substituted anilino group represented by Formula III:

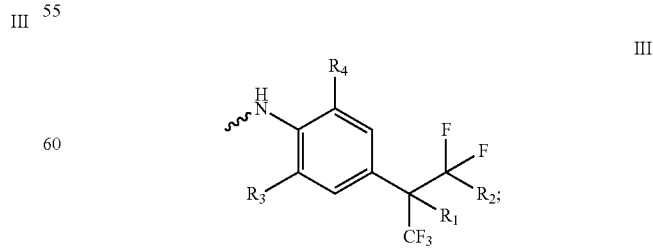

wherein $R_1$ is selected from methoxy or fluorine, $R_2$ is selected from fluorine or trifluoromethyl, $R_3$ is selected from any one of H, fluorine, chlorine, bromine, iodine, nitro or trifluoromethyl, and $R_4$ is selected from any one of trifluoromethyl, trifluoromethoxy or difluoromethoxy; and ⁓ represents the position at which the group is attached;

the molar ratio of the compound represented by Formula II to cyclopropyl formaldehyde is 1:(0.5-3); the mass ratio of the compound represented by Formula II to the acid is 1:(0.01-0.6);

the mass ratio of the compound represented by Formula II to the catalyst is 1:(0.001-0.05); and the mass ratio of the compound represented by Formula II to the solvent is 1:(2-10).

11. The method of claim 2 wherein the alkoxy group is selected from methoxy, ethoxy, propoxy or isopropoxy.

12. The method of claim 2 wherein the alkylamino group is a methylamino group.

13. The method according to claim 4 wherein the ester solvent includes any one or a combination of at least two selected from the group consisting of methyl acetate, ethyl acetate, propyl acetate and butyl acetate.

14. The method according to claim 4 wherein the ether solvent includes any one or a combination of at least two selected from the group consisting of diethyl ether, methyl tert-butyl ether and tetrahydrofuran.

15. The method according to claim 4 wherein the halogenated hydrocarbon solvent includes at least one of dichloromethane and dichlorethane.

16. The method according to claim 4 wherein the benzene solvent includes at least one of toluene and xylene.

17. The method according to claim 4 wherein the solvent includes any one or a combination of at least two selected from the group consisting of methanol, ethanol, ethyl acetate and toluene.

18. The method according to claim 5 wherein the acid is any one or a combination of at least two selected from the group consisting of formic acid, acetic acid, propionic acid, hydrochloric acid and sulfuric acid.

19. The method according to claim 5 wherein the acid is at least one of acetic acid and propionic acid.

20. The method of claim 6 wherein the catalyst includes platinum carbon.

21. The method of claim 7 wherein the molar ratio of the compound represented by Formula II to cyclopropyl formaldehyde is 1:(1.2-1.6).

22. The method of claim 7 wherein the mass ratio of the compound represented by Formula II to the acid is 1:(0.01-0.6).

23. The method of claim 22 wherein the mass ratio is 1:(0.05-0.4).

24. The method of claim 7 wherein the mass ratio of the compound represented by Formula II to the catalyst is 1:(0.001-0.05).

25. The method of claim 24 wherein the mass ratio is 1:(0.005-0.02).

26. The method of claim 7 wherein the mass ratio of the compound represented by Formula II to the solvent is 1:(2-10).

27. The method of claim 26 wherein the mass ratio is 1:(3-8).

28. The method of claim 8 wherein the temperature is 40-100° C.

29. The method of claim 8 wherein the hydrogenation reaction is carried out for 12-16 h.

30. The method of claim 9 wherein the pressure of the hydrogenation reaction after introducing hydrogen gas is controlled to 1.0-3.0 MPa.

\* \* \* \* \*